(12) United States Patent
Falcon et al.

(10) Patent No.: US 6,605,116 B2
(45) Date of Patent: Aug. 12, 2003

(54) REINFORCED RADIUS MAMMARY PROSTHESES AND SOFT TISSUE EXPANDERS

(75) Inventors: Anita M. Falcon, Euless, TX (US); Robert L. Guest, Colleyville, TX (US); Keith Job, Colleyville, TX (US); Steven Weir, Arlington, TX (US); Shijung Zhou, Southlake, TX (US)

(73) Assignee: Mentor Corporation, Santa Barbara, CA (US)

( * ) Notice: Subject to any disclaimer, the term of this patent is extended or adjusted under 35 U.S.C. 154(b) by 0 days.

(21) Appl. No.: 09/826,400

(22) Filed: Apr. 3, 2001

(65) Prior Publication Data

US 2002/0143396 A1 Oct. 3, 2002

(51) Int. Cl.[7] .............................. A61F 2/12; B29C 41/00
(52) U.S. Cl. ............................................ 623/8; 156/219
(58) Field of Search ...................... 623/7, 8; 156/215, 156/219, 220, 229

(56) References Cited

U.S. PATENT DOCUMENTS

| | | |
|---|---|---|
| 2,847,775 A | 7/1958 | Pangman |
| 3,189,921 A | 6/1965 | Pangman |
| 3,293,663 A | 12/1966 | Cronin |
| 3,366,975 A | 2/1968 | Pangman |
| 3,559,214 A | 2/1971 | Pangman |
| 3,665,520 A | 5/1972 | Perras et al. |
| 3,683,424 A | 8/1972 | Pangman |
| 3,700,380 A | 10/1972 | Kitrilakis |
| 4,125,117 A * | 11/1978 | Lee ................................ 623/7 |
| 4,264,990 A * | 5/1981 | Hamas ........................... 623/8 |
| 4,460,713 A | 7/1984 | Lee et al. |
| 4,499,211 A | 2/1985 | Walch et al. |
| 4,531,244 A | 7/1985 | Hamas |
| 4,576,608 A | 3/1986 | Homsy |
| 4,648,880 A | 3/1987 | Brauman |
| 4,820,303 A | 4/1989 | Brauman |
| 4,823,815 A * | 4/1989 | Watson et al. .................. 623/8 |
| 4,889,744 A | 12/1989 | Quaid |
| 4,919,659 A | 4/1990 | Horbett et al. |
| 4,936,858 A | 6/1990 | O'Keeffe |
| 4,955,907 A | 9/1990 | Ledergerber |
| 4,955,909 A | 9/1990 | Ersek et al. |

(List continued on next page.)

*Primary Examiner*—David J. Isabella
(74) *Attorney, Agent, or Firm*—Fish & Richardson P.C.

(57) ABSTRACT

The prosthesis of the invention are configured such that the average thickness of the shell in the region where the posterior and anterior faces meet is greater, e.g., at least twice, the average thickness of the shell in the region of the anterior face. This reinforcement can reduce or eliminate undesirable scalloping effects along the upper perimeter of the prosthesis that can otherwise occur when gravity pulls downward on a filled prosthesis. Moreover, because the reinforcement is preferably confined to a radius/posterior region extending at least part of the way around the perimeter of the prosthesis, it is possible for the shell of the prosthesis in nearly the entire anterior face of the prosthesis to be formed of relatively thin material. This preserves a natural appearance of the prosthesis when it is implanted.

35 Claims, 3 Drawing Sheets

U.S. PATENT DOCUMENTS

| | | | |
|---|---|---|---|
| 4,960,425 | A | 10/1990 | Yan et al. |
| 4,963,150 | A | 10/1990 | Brauman |
| 5,002,572 | A | 3/1991 | Picha |
| 5,007,929 | A | 4/1991 | Quaid |
| 5,011,494 | A | 4/1991 | von Recum et al. |
| 5,022,942 | A | 6/1991 | Yan et al. |
| 5,092,348 | A | 3/1992 | Dubrul et al. |
| 5,116,370 | A | 5/1992 | Foglietti |
| 5,141,581 | A | 8/1992 | Markham |
| 5,146,933 | A | 9/1992 | Boyd |
| 5,158,571 | A | 10/1992 | Picha |
| 5,171,269 | A | 12/1992 | Bark |
| 5,207,709 | A | 5/1993 | Picha |
| 5,219,360 | A | 6/1993 | Georgiade |
| 5,219,361 | A | 6/1993 | von Recum et al. |
| 5,236,453 | A | 8/1993 | Picha |
| 5,271,736 | A | 12/1993 | Picha |
| 5,282,856 | A | 2/1994 | Ledergerber |
| 5,296,069 | A | 3/1994 | Robert |
| 5,344,451 | A | 9/1994 | Dayton |
| 5,354,338 | A | 10/1994 | Ledergerber |
| 5,356,429 | A | 10/1994 | Seare |
| 5,383,929 | A | 1/1995 | Ledergerber |
| 5,425,762 | A | 6/1995 | Muller |
| 5,437,900 | A | 8/1995 | Kuzowski |
| 5,462,781 | A | 10/1995 | Zukowski |
| 5,480,430 | A | 1/1996 | Carlisle et al. |
| 5,522,896 | A | 6/1996 | Prescott |
| 5,525,275 | A | 6/1996 | Iversen et al. |
| 5,545,217 | A | 8/1996 | Offray et al. |
| 5,545,220 | A | 8/1996 | Andrews et al. |
| 5,564,439 | A | 10/1996 | Picha |
| RE35,391 | E | 12/1996 | Brauman |
| 5,630,843 | A | 5/1997 | Rosenberg |
| 5,630,844 | A | 5/1997 | Dogan et al. |
| 5,653,755 | A | 8/1997 | Ledergerber |
| 5,658,330 | A | 8/1997 | Carlisle et al. |
| 5,674,285 | A | 10/1997 | Quaid |
| 5,676,698 | A | 10/1997 | Janzen et al. |
| 5,713,960 | A | 2/1998 | Christensen et al. |
| 5,779,734 | A | 7/1998 | Ledergerber |
| 5,922,024 | A | 7/1999 | Janzen et al. |
| 5,961,552 | A | 10/1999 | Iversen et al. |
| 5,964,803 | A | 10/1999 | Iversen et al. |
| 5,993,590 | A | 11/1999 | Krotseng |
| 6,146,418 | A | 11/2000 | Berman |
| 6,162,251 | A | 12/2000 | Kredovski |
| 6,187,043 | B1 | 2/2001 | Ledergerber |
| 6,214,045 | B1 | 4/2001 | Corbitt, Jr. et al. |
| 6,228,116 | B1 | 5/2001 | Ledergerber |

\* cited by examiner

REINFORCED RADIUS MAMMARY PROSTHESES AND SOFT TISSUE EXPANDERS

TECHNICAL FIELD

This invention relates to implantable prostheses and tissue expanders, and more particularly to implantable mammary prostheses and soft tissue expanders.

BACKGROUND

Implantable prostheses are commonly used to replace or augment body tissue. In the case of the female breast, it sometimes necessary to remove some or all of the mammary gland and surrounding tissue in order to treat breast cancer. This surgery leaves a void that can be filled with an implantable prosthesis. The implant serves to support surrounding tissue and to maintain the appearance of the body. The restoration of the normal appearance of the body has an extremely beneficial psychological effect on post-operative patients, eliminating much of the shock and depression that often follows extensive surgical procedures. Implantable mammary prostheses are also used more generally for enlargement of the breast.

Implantable mammary prostheses are commonly formed of a silicone polymer shell and are filled with saline or some other fluid or gel.

SUMMARY

Implantable mammary prostheses generally have a relatively flat posterior face that is placed against the patient's chest and a domed anterior face. It is often desirable for the region where the anterior face meets the posterior face, the perimeter region, to have a relatively small radius of curvature, particularly at the upper pole of the prosthesis, i.e., the portion of the prosthesis that is uppermost when the patient is standing. A relatively narrow radius of curvature in the transition between the anterior face and the posterior face in the upper pole of the prosthesis is desirable because it permits a relatively smooth transition between the mammary tissue and the implant when the prosthesis is implanted. However, a small radius is sometimes associated with the appearance of creases that extend inward from the perimeter of the prosthesis in the region of relatively small radius. This is sometimes referred to as a scalloping effect. Scalloping tend to occur when the prosthesis is filled with fluid and the patient is upright such that the weight of the filling material is pulling downward on the prosthesis. The creases often appear on the anterior face of the prosthesis. This is aesthetically undesirable as the creases can sometimes be discerned through the overlying skin of the patient.

The prosthesis of the invention are configured such that the average thickness of the shell in the region where the posterior and anterior faces meet is greater, e.g., at least twice, the thickness of the shell in the region of the anterior face. Applicants have found that this reinforcement can reduce or eliminate undesirable scalloping effects. In some embodiments, the average thickness of the shell in the region of posterior face is also greater, e.g., at least twice, the thickness of the shell in the region of the anterior face. Moreover, because the reinforcement is preferably confined to the perimeter (or radius) of the shell and, optionally, posterior face of the shell, it is possible for nearly the entire anterior face of the prosthesis to be formed of relatively thin material. This preserves a natural appearance of the prosthesis when it is implanted.

The invention features an implantable prosthesis comprising an elastomeric shell having an anterior face, a posterior face, and a perimeter region where the anterior face and the posterior face meet, wherein the average thickness of the shell in at least a reinforced portion of the perimeter region is greater than the average thickness of the shell in the anterior face. In various preferred embodiments, the prosthesis is a mammary prosthesis, the average thickness of the shell in the reinforced portion of the perimeter region is about 0.02 to 0.08 inches, the average thickness of the shell in the entire perimeter region is greater than the average thickness of the shell in the anterior face, the average thickness of the posterior face of the shell is about 0.02 to 0.08 inches, the average thickness of the anterior face of the shell is less than about 0.04 inches, the average thickness of the anterior face of the shell is less than about 0.03 inches, the prosthesis includes a filling port, and the prosthesis is filled with a gel or a liquid.

The invention also features a kit comprising a prosthesis of the invention and a means for filling the prosthesis with a liquid or a gel. In a preferred embodiment, the filling means comprises a syringe and a tube adapted to connect the syringe to the filling port of the shell of the prosthesis.

The invention further features a method for forming a prosthesis, the method comprising: (a) providing a mandrel adapted for dip molding a mammary prosthesis, the mandrel having an anterior face, a posterior face and a perimeter region where the anterior face and the posterior face meet; (b) masking both the anterior face and the posterior face of the mandrel while leaving at least a portion of the perimeter region free of masking; (c) dipping the masked mandrel into a silicone dispersion at least one time; (d) removing the mandrel from the silicone dispersion; (e) removing the masking from the mandrel; and (f) dipping the unmasked mandrel into a silicone dispersion at least one time.

The invention also features a method for forming a prosthesis, the method comprising: (a) providing a mandrel adapted for dip molding a mammary prosthesis, the mandrel having an anterior face, a posterior face and a perimeter region where the anterior face and the posterior face meet; (b) masking the anterior face of the mandrel while leaving at least a portion of the perimeter region and the posterior face free of masking; (c) dipping the masked mandrel into a silicone dispersion at least one time; (d) removing the mandrel from the silicone dispersion; (e) removing the masking from the mandrel; and (f) dipping the unmasked mandrel into a silicone dispersion at least one time. In various embodiments, the masked mandrel is dipped into a silicone dispersion at least two times; and the unmasked mandrel is dipped into a silicone dispersion at least two times. In other embodiment a first portion of the masking is removed, the mandrel is dipped at least once, the remainder of the masking is removed and the mandrel is dipped again.

The invention also features a method for forming a prosthesis shell, the comprising: (a) dipping an appropriately sized and shaped mandrel into a silicone dispersion such that the posterior face and perimeter of the mandrel, but not the entire anterior face of the mandrel is submerged in the dispersion; (b) repeating step (a) until a desired partial thickness is achieved; (c) dipping the entire mandrel into the dispersion; and (d) repeating step (c) until a desired final thickness is achieved.

The invention also features a method for forming a reinforced mammary prosthesis, the method comprising: (a) forming an elastomeric mammary prosthesis shell, the shell having an inner surface, an outer surface, anterior face, a posterior face, and a perimeter region where the anterior face and the posterior face meet; and (b) adhering a sheet a of elastomeric material to the inner surface of the shell at the perimeter region.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

In the standard process for manufacturing surgical prosthesis, and particularly, mammary implants, a shell of desired thickness is formed having the desired shape for the particular implant and purpose. The shell may be single lumen or multilumen and is commonly formed of a biocompatible elastomer, e.g., silicone. Dip molding using an appropriately sized and shaped mandrel is commonly used to form the shell. The mandrel is dipped into a silicone dispersion and then removed to allow partial cure or solvent evaporation. The process is generally repeated several times. Once the shell has been formed it is removed from the mandrel. This dip molding process results in the formation of a partial shell that has an opening, e.g., a circular hole (patch hole) in its posterior face. The patch hole is subsequently covered with a patch that seals the hole, thus forming a complete, fluid impervious shell. The patch is attached to the partial shell using silicone rubber or other similar biocompatible adhesive. The patched shell is commonly provided with a fill port or valve, preferably in the posterior face of the prosthesis. The completed shell can either be non-filled or pre-filled or intraoperatively filled through the small fill port or valve with saline, gel, foam, or combinations of these materials or other suitable material known in the art to provide a complete fluid-filled prosthesis. The fill port or valve is sealed or closed, and the prosthesis is sterilized.

Figure 1:
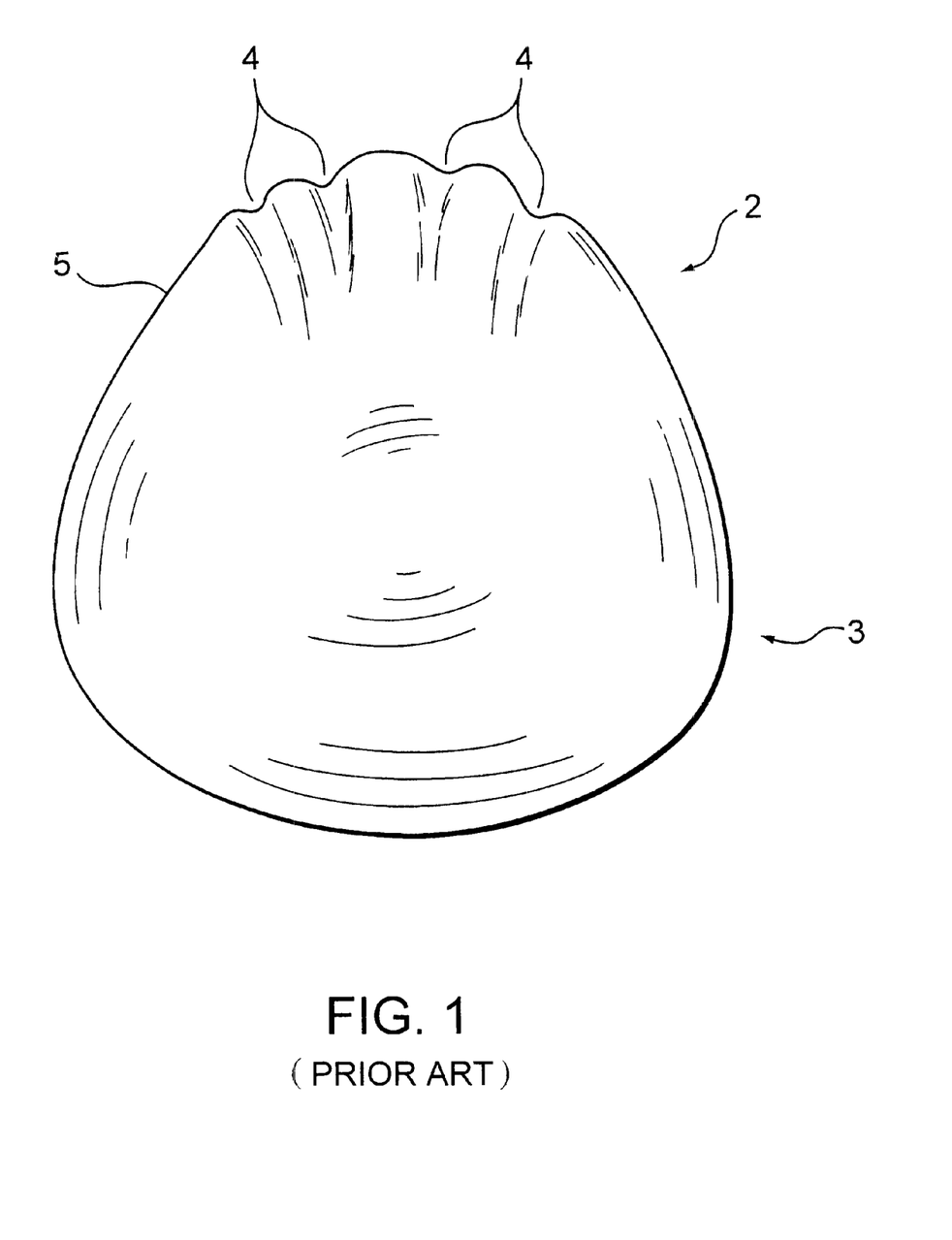
FIG. 1 is an anterior view of a prior art mammary prosthesis illustrating the appearance of radial creases (scalloping).

FIG. 1 shows an anterior view of a prior art mammary prosthesis depicting the creases that can form on the anterior face of the shell of the prosthesis when the prosthesis is filled and gravity is pulling downward on the prosthesis. This effect is sometimes referred as scalloping. The prosthesis has an upper pole 2 and a lower pole 3. Several creases 4 are shown on the upper pole of the anterior face and radiating inwardly from the perimeter 5 of the prosthesis. The creases formed in the anterior face can be discerned through the skin of the patient and are not aesthetically desirable.

Figure 2:
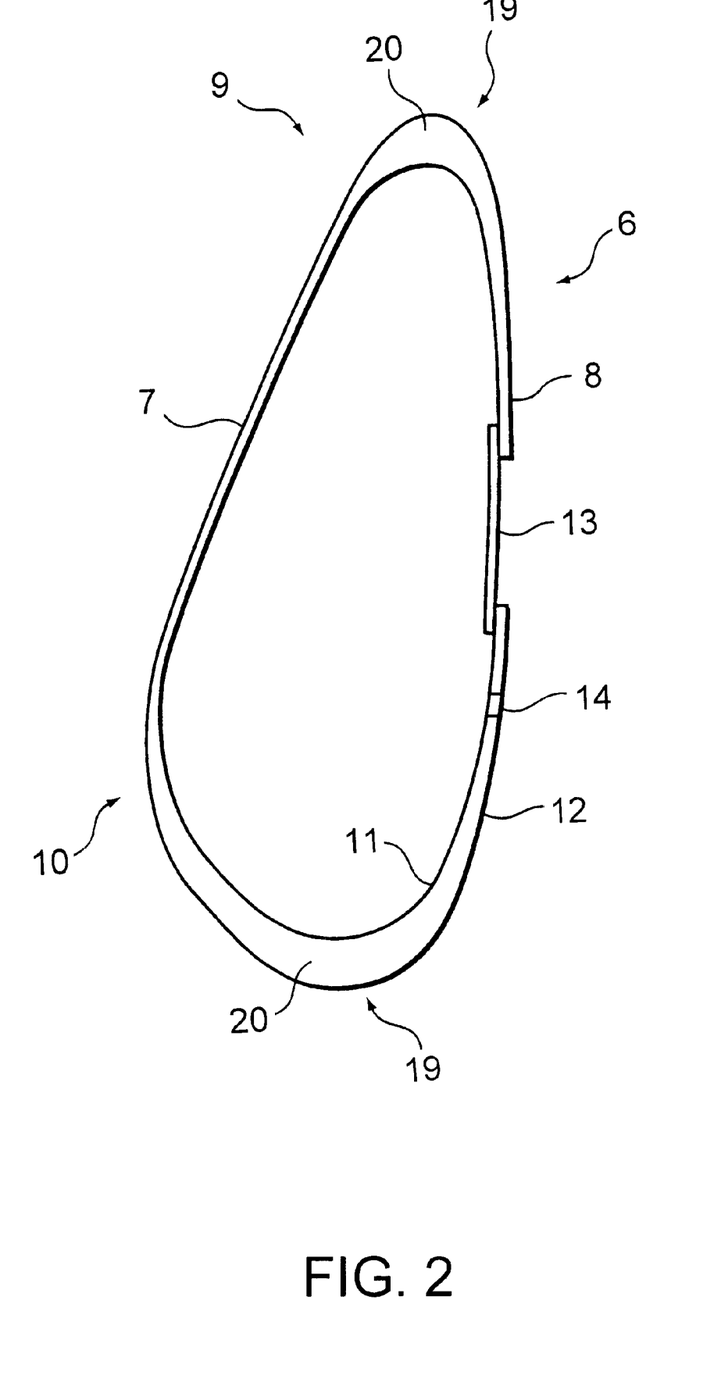
FIG. 2 is a cross-section view of an embodiment of the invention.

FIG. 2 shows a cross-section view of the shell 6 of a mammary prosthesis of the invention. The shell has an anterior face region 7, a posterior face region 8, an upper pole region 9 (i.e., the upper half of the shell when the prosthesis recipient is standing), a lower pole region 10 (i.e., the lower half of the shell when the prosthesis recipient is standing), an inner surface 11, an outer surface 12, a patch 13 and a filling port or valve 14 located on the posterior face region of the prosthesis. The posterior face region 8 of the shell is placed against the patient's chest wall when the prosthesis is implanted. As can be seen in FIG. 2, the perimeter region 19 of the shell where the anterior face region 7 and posterior face region 8 meet has a smaller radius of curvature in the region of the upper pole 9 than the lower pole 10. As can also be seen in FIG. 2 the shell is thicker in the perimeter region and posterior face region than in the anterior face region. In effect, the perimeter region and posterior face region are formed such that the shell is thicker in the perimeter region and posterior face region than in the anterior face region. Importantly, the thickened portion of the perimeter region extends somewhat onto the anterior face of the prosthesis and somewhat onto the posterior face of the prosthesis. Thus, the shell in a portion of the anterior face extending inward from the extreme outer limit of the line where the anterior face and posterior face meet is thicker than the shell in the remainder of the anterior face. There is preferably a smooth transition between the reinforced region and the anterior face region of the shell. This reinforcement 20 is preferably formed of the same material as the remainder of the shell. In the embodiment shown in FIG. 2 the reinforcement 20 extends around the entire perimeter of the prosthesis. This not need be the case. In other embodiments, the reinforcement extends only around a portion of the perimeter and posterior region of the shell (e.g., it extends for 40%–80% around the perimeter (or outer perimeter of the shell) centered at the apex of the upper pole.

Figure 3:
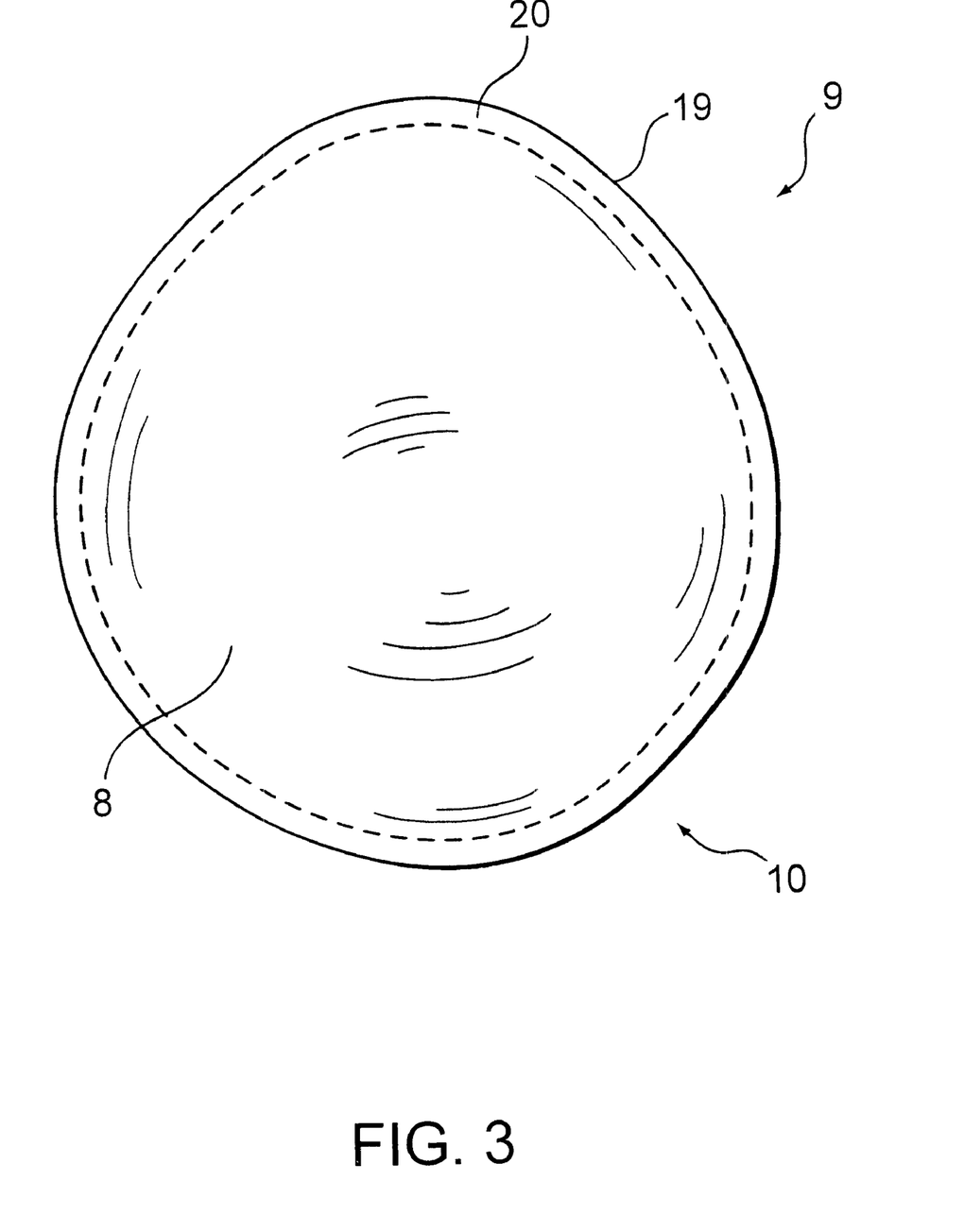
FIG. 3 is an anterior view of an embodiment of the invention.

FIG. 3 is an anterior view of a prosthesis of the invention. The prosthesis has an upper pole 9 and a lower pole 10. As can be seen in FIG. 3, the reinforcement 20 extends around the entire perimeter 19 of the prosthesis and is relatively narrow towards anterior face so that it extends only a small amount into the anterior face region. Thus, the vast majority of the anterior face region 7 of the shell can be desirably thin. For example, the average thickness of the shell in the anterior face region can be about one half that of the reinforced portion of the perimeter region. In this embodiment, the posterior face region of the shell is thicker than the anterior face region of the shell.

Measuring from the extreme outer edge of where the anterior face and posterior face meet, the reinforcement preferably extends 0.5–2.0 inches towards the anterior face of the shell from the point where the anterior and posterior faces meet (the extreme outer perimeter of the prosthesis), more preferably 0.5–1.5 inches. It is desirable that there be relatively smooth transition from the reinforced region to the anterior face of the shell. Preferably, the transition is such that, when the prosthesis is filled for implantation, the transition cannot be felt on the exterior surface of the shell. The longitudinal axis of the reinforcement follows the perimeter (circumference) of the prosthesis and is centered at the line where the anterior and posterior faces meet. The entire posterior face region of the shell can also be thicker than the anterior face region of the shell. Thus, the shell in the posterior region can be at least twice as thick (or thicker) than the shell in the perimeter face region.

Preferably, the entire perimeter of the prosthesis is reinforced. However, it is possible to reinforce only the upper pole, e.g., the upper half of the prosthesis. In addition, the reinforcement can extend only 30%, 50%, 70%, or 90% around the perimeter of the prosthesis. Generally, the reinforcement extends around the perimeter equidistant from the center of the upper pole of the prosthesis. It has been found that this narrow reinforced region will not only prevent scalloping in the region where the anterior and posterior faces meet, but will also reduce or prevent the formation of undesirable folds or valleys on the anterior face of the shell. Folds or valleys on the anterior face can create an undesirable wavy appearance of the breast in which the implant is inserted. The narrow reinforced region has this beneficial effect despite that fact that reinforced region does not extend substantially onto anterior face of the prosthesis. Accordingly, nearly all of the anterior face of the prosthesis is relatively thin. This is significant because the thinness of the shell on the anterior face of the prosthesis is an important aesthetic factor since, without significant soft tissue coverage, it can be felt through skin.

The shell of the prosthesis of the invention is generally at least 0.01 to 0.10 inches thick. The anterior face of the shell is generally 0.01 to 0.04 inches thick on average, preferably about 0.014 to 0.030 inches thick on average. The reinforced region (which can include just the perimeter of the shell or the perimeter of the shell and the posterior face) of the shell is generally 0.03 to 0.10 inches thick on average, preferably 0.04 to 0.08 inches thick on average. Thus, the average thickness of the reinforced region of the shell is at least about 1.5 to 2.5 times, preferably about 2 times the average thickness of the anterior face of the shell.

The prosthesis of the invention can be produced by any suitable means. For example, a layer of material can be attached to a pre-formed shell in order to form a reinforced region. Alternatively, a shell with a reinforced region can be prepared without separately forming a shell and a reinforcement layer. For example, the reinforced shell can be prepared by dip molding and masking or controlled partial/full dip molding. The reinforced shell can also be formed by injection molding using an appropriately sized and shaped mold. The shell can also be formed by controlled spraying of a silicone dispersion on a mandrel.

EXAMPLE 1

An elastomeric shell with a reinforced perimeter region is formed by first preparing an unreinforced shell and then applying a reinforcement layer.

An elastomeric shell is formed by conventional dip-molding in silicone dispersion using an appropriately sized and shaped mandrel. The shell will generally have an opening on its posterior face in order to strip it off the mandrel. The shell is formed of medical grade silicone rubber. The cured shell is then turned inside out and stretched over an appropriately shaped and sized disk that allows the perimeter of the shell to lie smooth. The reinforced region is created by placing a piece of unvulcanized silicone rubber along the portion of the perimeter of the shell to be reinforced. Preferably the reinforcement sheeting is placed on the interior surface of the shell. The shell is next carefully removed from the disk such that the uncured reinforcement sheeting does not come into contact with portions of the shell that are not to be reinforced.

The opening in the posterior face of the shell is sealed using a patch comprising a vulcanized layer of silicone sheeting and an unvulcanized layer of silicone. The patch is shaped and sized to be somewhat larger than the opening in the posterior face of the shell. The patch is positioned inside the shell such that the unvulcanized layer of the patch faces outward and the perimeter of the patch overlaps the edge of the shell surrounding the opening. The assembly is compressed either between hot platens at, e.g., 325° F. and 60 p.s.i. or platens at room temperature and 60 p.s.i. for about two to three minutes. The patched shell is then cured in an oven at 325° F. for about one half hour to cure fully.

EXAMPLE 2

An elastomeric shell with a reinforced perimeter is formed by dip molding with masking. The mandrel used for dip molding has the general shape of a mammary prosthesis. Thus, it has an anterior face, a posterior face and a perimeter where the anterior and posterior faces meet.

An appropriately sized and shaped mandrel is masked such that the only non-masked region is the portion corresponding to the perimeter of the shell. Thus, the regions corresponding to the anterior and posterior faces of the shell are masked. The reinforced perimeter region is then built up by several cycles of dipping until the desired thickness is achieved. The masks are then removed before they become buried in the cured shell. The remainder of the shell (the posterior face and the anterior face) is then built up by several cycles of dipping. It is also possible to first remove the mask covering the region of the mandrel corresponding to the posterior surface of the shell, perform one or more cycles of dipping and then remove the mask covering the region of the mandrel corresponding to the anterior surface of the shell and perform one or more additional cycles of dipping. This allows the posterior face region of the shell to be thicker than the anterior face region of the shell. As discussed above, the shell will have an opening in its posterior face in order to strip it off the mandrel. The shell can be assembled into a device as discussed in Example 1.

EXAMPLE 3

An elastomeric shell with a reinforced perimeter region and posterior region is formed by a controlled combination of partial/full dip-molding process. This process permits one to use dip casting to prepare a shell of varying thickness without the need for masking.

An appropriately sized and shaped mandrel is dipped into a silicone dispersion such that only the portion of mandrel approximately 0.5" above the radius (perimeter) of the mandrel is exposed in the air. The reinforced region, which here includes the perimeter and the posterior face, is built up by several cycles of partial dipping until the desired partial thickness is achieved.

The remainder of the shell is then built up by several cycles of full dipping in which the whole mandrel is submerged in the dispersion. During these full dips the entire shell is made thicker, and the full dips continue until the entire desired thickness of the shell is achieved. As discussed above, the shell will have an opening in its posterior face in order to strip it off the mandrel. The shell can be assembled into a device as discussed in Example 1.

Other Embodiments

The shell can be circular, oval, or crescent shaped. The exterior surface of the shell can be smooth or textured. The prosthesis can have a single lumen or multiple lumens. It can be formed of silicone rubber, a laminate of various forms of silicone, silicone copolymers, polyurethane, and various other elastomers in various combinations. Various materials are described in U.S. Pat. Nos. 4,592,755 and 4,205,401.

The shell can be filled with a fluid or gel. In addition, an amount of solid material can be combined with the fluid or gel to adjust the density or compressibility of the filling.

If desired, all or part of the exterior surface of the shell may be textured e.g., as described in U.S. Pat. No. 4,960,425, herein incorporated by reference. As explained in greater detail in U.S. Pat. No. 4,960,425, a textured shell can be formed by disposing a shell having a smooth exterior surface on a flattened or slightly curved disk and coating all or part of the exterior surface of the shell with unvulcanized or partially vulcanized silicone. The unvulcanized silicone layer is then covered with a porous or textured medium and the entire combination is compressed between platens for a short time until a textured surface is formed in the silicone layer. The textured shell is then cured. After curing, the patch hole is covered with a patch that can optionally be texturized utilizing a similar procedure. Alternatively, a mandrel in the shape of the prosthesis and having a texturized surface is coated with silicone rubber or other polymeric biocompatible material. A shell is then disposed on the mandrel and the coating is cured on the shell. The texturized shell is removed from the mandrel, turned inside out and then patched and filled. As another alternative, the shell can be directly molded on a mold having a textured surface on at least one side. The formed shell is then turned inside out to expose the textured surface on the outside of the shell.

In general, a textured or texturized surface is one having minute indentations, deformations and/or raised portions on the subject surface. The width of each individual raised portion or indentation generally ranges in size from 0.0003 to 0.10 inches. The depth of the indentations and raised portions is on the order of 0.0003 to 0.030 inches. Thus, the general appearance of the prosthesis is that of an opaque surface, slightly rough to the touch. Preferably only the posterior face region of the shell is textured while the anterior face region is substantially smooth.

Mammary tissue expanders, which are generally implanted for only a few weeks or months rather than a year or more can also be formed with a reinforced perimeter region. This will substantially prevent scalloping while allowing the shell of the tissue expander in the anterior face region to be desirably thin. Many types of prostheses other than mammary prostheses can also be formed with a reinforced perimeter region.

The prosthesis of the invention can be provided as a kit with a shell and a means for filling the shell, e.g., a syringe. The kit can further include an adapter tube for connecting the syringe to the filling port of the shell.

A number of embodiments of the invention have been described. Nevertheless, it will be understood that various modifications may be made without departing from the spirit and scope of the invention.

What is claimed is:

1. An implantable prosthesis comprising an elastomeric shell having an anterior face, a posterior face, a perimeter region where the anterior face and the posterior face meet, and a smoothly curved transition between the posterior face and the anterior face, wherein the average thickness of the shell in at least a reinforced portion of the perimeter region is greater than the average thickness of the shell in the anterior face, wherein the reinforced portion of the perimeter region extends less than 2 inches, but more than 0.5 inches onto the anterior face of the prosthesis, and wherein there is a smooth transition between the reinforced portion of the perimeter region and the anterior face of the shell on the exterior surface of the shell.

2. The prosthesis of claim 1 wherein the reinforced portion of the perimeter region extends less than 1.5 inches, but more than 0.5 inches onto the anterior face of the prosthesis.

3. An implantable prosthesis comprising an elastomeric shell having an anterior face, a posterior face, a perimeter region where the anterior face and the posterior face meet, and a smoothly curved transition between the posterior face and the anterior face, wherein the average thickness of the shell in at least a reinforced portion of the perimeter region is greater than the average thickness of the shell in the anterior face, wherein the reinforced portion of the perimeter region extends no more than 0.5 inches onto the anterior face of the prosthesis, and wherein there is a smooth transition between the reinforced portion of the perimeter region and the anterior face of the shell on the exterior surface of the shell.

4. The prosthesis of any of claims 1–2 wherein the prosthesis is a mammary prosthesis.

5. The prosthesis of any of claims 1–2 wherein the average thickness of the shell in the reinforced portion of the perimeter region is about 0.02 to 0.08 inches.

6. The prosthesis of claim of any of claims 1–2 wherein the average thickness of the shell in the entire perimeter region is greater than the average thickness of the shell in the anterior face.

7. The prosthesis of any of claims 1–2 wherein the average thickness of the posterior face of the shell is about 0.02 to 0.08 inches.

8. The prosthesis of any of claims 1–2 wherein the average thickness of the anterior face of the shell is less than about 0.04 inches.

9. The prosthesis of claim 8 wherein the average thickness of the anterior face of the shell is less than about 0.03 inches.

10. The prosthesis of any of claims 1–2 wherein the prosthesis is filled with a gel or a liquid.

11. The prosthesis of any of claims 1–2 wherein at least a portion of the posterior face of the shell is textured.

12. The prosthesis of any of claims 1–2 wherein at least a portion of the anterior face of the shell is textured.

13. The prosthesis of claim 12 wherein at least a portion of the posterior face of the shell is textured.

14. The prosthesis of claim 11 wherein the entire posterior face of the shell is textured.

15. The prosthesis of claim 12 wherein the entire anterior face of the shell is textured.

16. The prosthesis of claim 15 wherein the entire posterior face of the shell is textured.

17. The prosthesis of an of claims 1–2 wherein the reinforced portion extends around no more than 90% of the perimeter region.

18. The prosthesis of an of claims 1–2 wherein the reinforced portion extends around no more than 70% of the perimeter region.

19. The prosthesis of any of claims 1–2 wherein the reinforced portion extends around no more than 50% of the perimeter region.

20. The prosthesis of any of claims 1–2 wherein the reinforced portion extends around no more than 30% of the perimeter region.

21. A kit comprising the prosthesis of any of claims 1–2 the shell of the prosthesis further comprising a filling port, the kit further comprising a means for filling the prosthesis with a liquid or a gel.

22. The kit of claim 21 wherein the filling means comprises a syringe and a tube adapted to connect the syringe to the filling port of the shell of the prosthesis.

23. A method for forming a prosthesis, comprising:
(a) providing a mandrel adapted for dip molding a mammary prosthesis, the mandrel having an anterior face, a posterior face and a perimeter region where the anterior face and the posterior face meet;
(b) masking both the anterior face and the posterior face of the mandrel while leaving at least a portion of the perimeter region free of masking, wherein the perimeter region free of masking extends less than 2 inches but more than 0.5 inches onto the anterior face of the prosthesis;

(c) dipping the masked mandrel into a silicone dispersion at least one time;

(d) removing the mandrel from the silicone dispersion;

(e) removing the masking from the mandrel; and (f) dipping the unmasked mandrel into a silicone dispersion at least one time.

24. A method for forming a prosthesis, comprising:

(a) providing a mandrel adapted for dip molding a mammary prosthesis, the mandrel having an anterior face, a posterior face and a perimeter region where the anterior face and the posterior face meet;

(b) masking the anterior face of the mandrel while leaving at least a portion of the perimeter region and the posterior face free of masking, wherein the perimeter region free of masking extends less than 2 inches but more than 0.5 inches onto the anterior face of the prosthesis;

(c) dipping the masked mandrel into a silicone dispersion at least one time;

(d) removing the mandrel from the silicone dispersion;

(e) removing the masking from the mandrel; and (f) dipping the unmasked mandrel into a silicone dispersion at least one time.

25. The method of claim 23 or 24 wherein the perimeter region free of masking extends less than 1.5 inches, but more than 0.5 inches onto the anterior face of the mandrel.

26. A method for forming a prosthesis, comprising:

(a) providing a mandrel adapted for dip molding a mammary prosthesis, the mandrel having an anterior face, a posterior face and a perimeter region where the anterior face and the posterior face meet;

(b) masking both the anterior face and the posterior face of the mandrel while leaving at least a portion of the perimeter region free of masking, wherein the perimeter region free of masking extends no more than 0.5 inches onto the anterior face of the prosthesis;

(c) dipping the masked mandrel into a silicone dispersion at least one time;

(d) removing the mandrel from the silicone dispersion;

(e) removing the masking from the mandrel; and (f) dipping the unmasked mandrel into a silicone dispersion at least one time.

27. A method for forming a prosthesis, comprising:

(a) providing a mandrel adapted for dip molding a mammary prosthesis, the mandrel having an anterior face, a posterior face and a perimeter region where the anterior face and the posterior face meet;

(b) masking the anterior face of the mandrel while leaving at least a portion of the perimeter region and the posterior face free of masking, wherein the perimeter region free of masking extends no more than 0.5 inches onto the anterior face of the prosthesis;

(c) dipping the masked mandrel into a silicone dispersion at least one time;

(d) removing the mandrel from the silicone dispersion;

(e) removing the masking from the mandrel; and (f) dipping the unmasked mandrel into a silicone dispersion at least one time.

28. The method of any of claims 23–27 wherein the masked mandrel is dipped into a silicone dispersion at least two times.

29. The method of any of claims 23–27 wherein the unmasked mandrel is dipped into a silicone dispersion at least two times.

30. A method for forming a prosthesis shell, comprising:

(a) dipping an appropriately sized and shaped mandrel into a silicone dispersion such that the posterior face and perimeter of the mandrel, but not the entire anterior face of the mandrel is submerged in the dispersion, wherein the portion of the anterior face that is submerged in the dispersion extends less than 2 inches, but more than 0.5 inches from the perimeter of the mandrel onto the anterior face;

(b) repeating step (a) until a desired partial thickness is achieved;

(c) dipping the entire mandrel into the dispersion;

(d) repeating step (c) until a desired final thickness is achieved.

31. The method of claim 30 wherein the portion of the anterior face that is submerged in the dispersion extends less than 0.5 inches, but more than 0.5 inches from the perimeter of the mandrel onto the anterior face.

32. A method for forming a prosthesis shell, comprising:

(a) dipping an appropriately sized and shaped mandrel into a silicone dispersion such that the posterior face and perimeter of the mandrel, but not the entire anterior face of the mandrel is submerged in the dispersion, wherein the portion of the anterior face that is submerged in the dispersion extends no more than 1.5 inches from the perimeter of the mandrel onto the anterior face;

(b) repeating step (a) until a desired partial thickness is achieved;

(c) dipping the entire mandrel into the dispersion;

(d) repeating step (c) until a desired final thickness is achieved.

33. A method for forming a reinforced mammary prosthesis, comprising:

(a) forming an elastomeric mammary prosthesis shell, the shell having an inner surface, an outer surface, anterior face, a posterior face, a perimeter region where the anterior face and the posterior face meet and a smoothly curved transition between the posterior face and the anterior face of the shell; and (b) adhering a sheet a of elastomeric material to the inner surface of the shell at the perimeter region, wherein the elastomeric material adhered to the perimeter region extends less than 2 inches, but more than 0.5 inches onto the anterior face of the prosthesis.

34. The method of claim 33 wherein the elastomeric material to the perimeter region extends less than 1.5 inches, but more than 0.5 inches onto the anterior face of the prosthesis.

35. A method for forming a reinforced mammary prosthesis, comprising:

(a) forming an elastomeric mammary prosthesis shell, the shell having an inner surface, an outer surface, anterior face, a posterior face, a perimeter region where the anterior face and the posterior face meet and a smoothly curved transition between the posterior face and the anterior face of the shell; and (b) adhering a sheet a of elastomeric material to the inner surface of the shell at the perimeter region, wherein the elastomeric material adhered to the perimeter region extends no more than 0.5 inches onto the anterior face of the prosthesis.

* * * * *

UNITED STATES PATENT AND TRADEMARK OFFICE
CERTIFICATE OF CORRECTION

PATENT NO. : 6,605,116 B2
DATED : August 12, 2003
INVENTOR(S) : Steven Weir et al.

It is certified that error appears in the above-identified patent and that said Letters Patent is hereby corrected as shown below:

Title page,
Item [56], References Cited, U.S. PATENT DOCUMENTS, replace "2,847,775" with -- 2,842,775 --

Column 8,
Lines 9, 11, 14, 18, 21, 26, 28, 30, 40, 43, 46, 49 and 52, replace "1-2" with -- 1-3 --
Lines 38 and 41, replace "an" with -- any --

Column 9,
Line 16, after "inches" insert -- , --

Column 10,
Line 18, replace first occurrence of "0.5" with -- 1.5 --
Line 27, replace "1.5" with -- 0.5 --

Signed and Sealed this

Twentieth Day of July, 2004

JON W. DUDAS
*Acting Director of the United States Patent and Trademark Office*